United States Patent
Bonne et al.

(10) Patent No.: US 7,476,852 B2
(45) Date of Patent: Jan. 13, 2009

(54) IONIZATION-BASED DETECTION

(75) Inventors: Ulrich Bonne, Hopkins, MN (US); Teresa M. Marta, White Bear Lake, MN (US); Karen M. Newstrom-Peitso, Hopkins, MN (US)

(73) Assignee: Honeywell International Inc., Morristown, NJ (US)

( * ) Notice: Subject to any disclaimer, the term of this patent is extended or adjusted under 35 U.S.C. 154(b) by 249 days.

(21) Appl. No.: 11/328,735

(22) Filed: Jan. 10, 2006

(65) Prior Publication Data

US 2006/0289809 A1 Dec. 28, 2006

Related U.S. Application Data

(60) Provisional application No. 60/681,776, filed on May 17, 2005.

(51) Int. Cl.
*G01J 3/10* (2006.01)
*G01N 30/02* (2006.01)
*G01N 27/66* (2006.01)
*H01J 27/20* (2006.01)

(52) U.S. Cl. ......... 250/288; 250/281; 250/283; 250/423 P; 250/504 R; 73/23.2; 73/23.22; 73/23.35; 73/23.41; 422/83; 436/161; 96/101; 95/82

(58) Field of Classification Search .......... 250/423 P, 250/504 R, 281–288; 73/23.2, 23.22, 23.31, 73/23.35, 23.36, 23.4, 23.24, 31.05, 30.3, 73/863.12; 422/70, 68.1, 82.03, 83; 96/101–107; 95/82–89; 436/161
See application file for complete search history.

(56) References Cited

U.S. PATENT DOCUMENTS

| | | | | |
|---|---|---|---|---|
| 4,476,392 | A | | 10/1984 | Young |
| 4,521,225 | A | * | 6/1985 | Jenkins et al. ............... 95/18 |
| 4,733,086 | A | * | 3/1988 | Simmonds ............ 250/423 P |
| 4,944,921 | A | * | 7/1990 | Colby et al. ............... 422/70 |
| 5,092,218 | A | * | 3/1992 | Fine et al. ................. 86/50 |
| 5,345,809 | A | * | 9/1994 | Corrigan et al. .......... 73/23.2 |
| 5,393,979 | A | * | 2/1995 | Hsi ....................... 250/382 |
| 5,551,278 | A | * | 9/1996 | Rounbehler et al. ....... 73/1.06 |
| 5,561,344 | A | * | 10/1996 | Hsi ....................... 313/494 |
| 5,611,846 | A | * | 3/1997 | Overton et al. ............ 96/102 |

(Continued)

FOREIGN PATENT DOCUMENTS

DK DD290268 A5 5/1991

(Continued)

OTHER PUBLICATIONS

PID, "Photoionization Detector" (Jun. 14, 1997) <http://www.shsu.edu/~chemistry/PID/PID.html>.*

(Continued)

*Primary Examiner*—Bernard E Souw
(74) *Attorney, Agent, or Firm*—Kris T. Fredrick

(57) ABSTRACT

Embodiments of the present invention relate to detector structures for use in a micro gas analyzer, preferably in a differential setup. The detector structures may comprise one or more detector types, such as photo-ionization (PID), electron capture (ECD), ion mobility (IMS), differential mobility (DMS), ion-trap mass spectrometer (ITMS), in which all are provided with ions and electrons from one vacuum ultra violet (VUV) source. This source may also provide ions for ion-based gas pumps.

20 Claims, 5 Drawing Sheets

U.S. PATENT DOCUMENTS

| | | | |
|---|---|---|---|
| 6,011,258 A * | 1/2000 | Baumbach et al. | 250/286 |
| 6,027,890 A * | 2/2000 | Ness et al. | 435/6 |
| 6,171,378 B1 * | 1/2001 | Manginell et al. | 96/143 |
| 6,386,014 B1 * | 5/2002 | Butch | 73/23.35 |
| 6,393,894 B1 | 5/2002 | Bonne et al. | |
| 6,448,777 B1 * | 9/2002 | Abdel-Rahman et al. | 324/464 |
| 6,457,347 B1 * | 10/2002 | Koo et al. | 73/23.35 |
| 6,646,444 B2 | 11/2003 | Dolgov et al. | |
| 6,792,794 B2 | 9/2004 | Bonne et al. | |
| 6,837,118 B2 | 1/2005 | Bonne et al. | |
| 6,974,706 B1 * | 12/2005 | Melker et al. | 436/518 |
| 7,100,421 B1 * | 9/2006 | Herring | 73/23.35 |
| 7,104,112 B2 * | 9/2006 | Bonne | 73/23.25 |
| 7,223,970 B2 * | 5/2007 | Miller et al. | 250/291 |
| 2003/0106363 A1 * | 6/2003 | Sacks et al. | 73/23.35 |
| 2003/0108448 A1 * | 6/2003 | Sacks et al. | 422/89 |
| 2003/0109054 A1 * | 6/2003 | Sacks et al. | 436/161 |
| 2004/0081581 A1 * | 4/2004 | Mount et al. | 422/61 |
| 2004/0224422 A1 * | 11/2004 | Bonne et al. | 436/177 |
| 2004/0245993 A1 * | 12/2004 | Bonne | 324/464 |
| 2005/0007119 A1 | 1/2005 | Belyakov et al. | |
| 2005/0042139 A1 * | 2/2005 | Bonne | 422/68.1 |
| 2005/0063865 A1 * | 3/2005 | Bonne et al. | 422/68.1 |
| 2005/0142662 A1 * | 6/2005 | Bonne | 436/149 |
| 2005/0239206 A1 * | 10/2005 | Mango | 436/31 |
| 2006/0194280 A1 * | 8/2006 | Dillon et al. | 435/69.1 |
| 2006/0262303 A1 * | 11/2006 | Bonne et al. | 356/328 |
| 2006/0289809 A1 * | 12/2006 | Bonne et al. | 250/504 R |
| 2007/0005254 A1 * | 1/2007 | Nilsson et al. | 702/19 |
| 2007/0028670 A1 * | 2/2007 | Bonne et al. | 73/31.05 |
| 2007/0095125 A1 * | 5/2007 | Bonne et al. | 73/23.35 |
| 2007/0113642 A1 * | 5/2007 | Bonne et al. | 73/204.11 |

FOREIGN PATENT DOCUMENTS

| | | |
|---|---|---|
| EP | 1178309 A1 | 2/2002 |
| WO | WO-9811432 | 3/1999 |

OTHER PUBLICATIONS

ECD, "Electron Capture Detector" (Sep. 2, 2000) <http://elchem.kaist.ac.kr/vt/chem-ed/sep/gc/detector/ecd.htm>.*

Wentworth, W. E., et al., "Non-radioactive electron-capture detector", *Journal of Chromatography A*, Elsevier, Amsterdam, NL, vol. 842, No. 1-2, (May 21, 1999), 229-266.

"Magnesium Fluoride (MgF2)", http://www.crystaltechno.com/Materials/MgF2.htm, (No date listed),1.

"Magnesium Fluoride (MgF2) Specialist Data Sheet", http://www.crystran.co.uk/products.asp?productid=203, (Dec. 16, 2005),1-4.

Bonne, U., et al., "Micro Gas Chromatography Tradeoff Study", UTC No.: AFRL-PR-WP-TR-2004-2060; Contract No. 03-S530-0013-01-C1, (Nov. 2003),1-54.

Dolgov, Boris N., "Sensors: New Developments and Applications—Poster", *Subminiature Photoionization VOC Sensor*, (2005),1.

Dolgov, B., "Subminature Photoionization VOC Sensor", *PittCon 2005*, (2005),1-11.

Moskowitz, Bruce M., "Fundamental Physical Constants and Conversion Factors", *Global earth physics a handbook of physical constants.*, Edited by Thomas J. Ahrens http://www.agu.org/reference/gephys/23_moskowitz.pdf,(1995),346-355.

Nazarov, Erkinjon G., "Microscale Drift Tubes for Ion Mobility Spectrometry", *Chemical Sensors & Interfacial Design, Gordon Research Conferences*,(2003).

* cited by examiner

IONIZATION-BASED DETECTION

RELATED APPLICATIONS

This application claims priority to U.S. Provisional Application Ser. No. 60/681,776 (entitled MICRO FLUID ANALYZER, filed May 17, 2005) which is incorporated herein by reference.

GOVERNMENT FUNDING

This invention was made with Government support under Agency Contract Number FA8650-04-C-2502 awarded by the United States Department of AFRL Wight Lab. The Government has certain rights in this invention.

FIELD OF THE INVENTION

Embodiments of the present invention relate to ionization based-detection for micro analyzers. More specifically, the embodiments of the present invention relate to detector structures and detection methods for micro gas chromatographs (GC).

BACKGROUND

Micro analyzers, such as micro gas chromatographs, allow for a versatility and adaptability in detection techniques not found in conventional analyzers. Due to their small size and portability, micro analyzers can perform laboratory procedures on-site, in locations that significantly larger traditional instruments are unable to, providing practical detection results of numerous types of samples. Micro analyzers may be used in environmental or military applications, such as on vehicles or equipment, for example. Micro analyzers may also be utilized in processing as an in-line detection instrument or as a batch analyzer.

Micro analyzers, such as a micro gas chromatograph, have several limitations. Some types of detectors used in such an analyzer rely on radioactive sources, which are of environmental concern. In addition, some detectors utilized require a high start or "ignition" voltage that can cause noise and interference with electronics or other proximately located sensors. When trying to use multiple detectors in a single device, high energy input is of concern, as well as the possibility of differing pressure requirements for different types of detectors.

SUMMARY

Embodiments of the present invention relate to a detector structure for use with or without a micro gas analyzer that is able to separate a sample gas mixture into its individual gas components. The detector structure comprises a photo-ionization detector (PID), an electron capture detector (ECD) and a vacuum ultra violet (VUV) source as an ionization source for both the PID and ECD. Further embodiments include a detector structure comprising two photo-ionization detectors (PID), two electron capture detectors (ECD), a vacuum ultra violet (VUV) source and the micro gas analyzer. The VUV source is an ionization source for both the inlet and outlet PIDs and ECDs, used in a differential detection mode, wherein the PIDs and ECDs utilize the same VUV source for ionization. The VUV may also provide ions for operation of microdischarge detectors (MDDs), ion trap mass spectrometers (ITMSs) and certain ion-based gas pumps.

DETAILED DESCRIPTION

References in the specification to "one embodiment," "an embodiment," "an example embodiment," indicate that the embodiment described may include a particular feature, structure, or characteristic, but every embodiment may not necessarily include the particular feature, structure, or characteristic. Moreover, such phrases are not necessarily referring to the same embodiment. Further, when a particular feature, structure, or characteristic is described in connection with an embodiment, it is submitted that it is within the knowledge of one skilled in the art to affect such feature, structure, or characteristic in connection with other embodiments whether or not explicitly described.

Embodiments of the present invention relate to a multidimensional detector structure by integration of detectors based on thermal conductivity (TC), photo-ionization (PI), ion-mobility (IM), electron capture (EC), and ion trap mass spectrometry (ITMS), for example. The detector structure may be used as a stand alone detector system in conjunction with any type of instrumental analysis device or as part of a micro analyzer, such as a micro gas chromatograph. The sample analyzed may be a liquid, gas or some combination of the two. The micro analyzer, such as a gas chromatograph, may heat the sample so that only gas contacts the detectors. A vacuum ultra violet (VUV) light is utilized as the photon and electron source by photo-ionization for one or more of the detectors integrated in the micro analyzer. The VUV light may also be used as the source for an ion drag pump used to mobilize the sample or analyte through the micro analyzer. The use of a VUV light replaces the need for environmentally sensitive radioactive sources or high temperature and energy thermionic emission sources. The utilization of a VUV light also simplifies the design and manufacture of the micro analyzer and the ignition voltage of detectors, such as a microdischarge detector (MMD), is also significantly reduced. The size of the VUV source (on the millimeter scale) may be large compared to the about 100-150-micrometer channels and about 10-100 micrometer detectors that are utilized in a micro analyzer.

Figure 1:
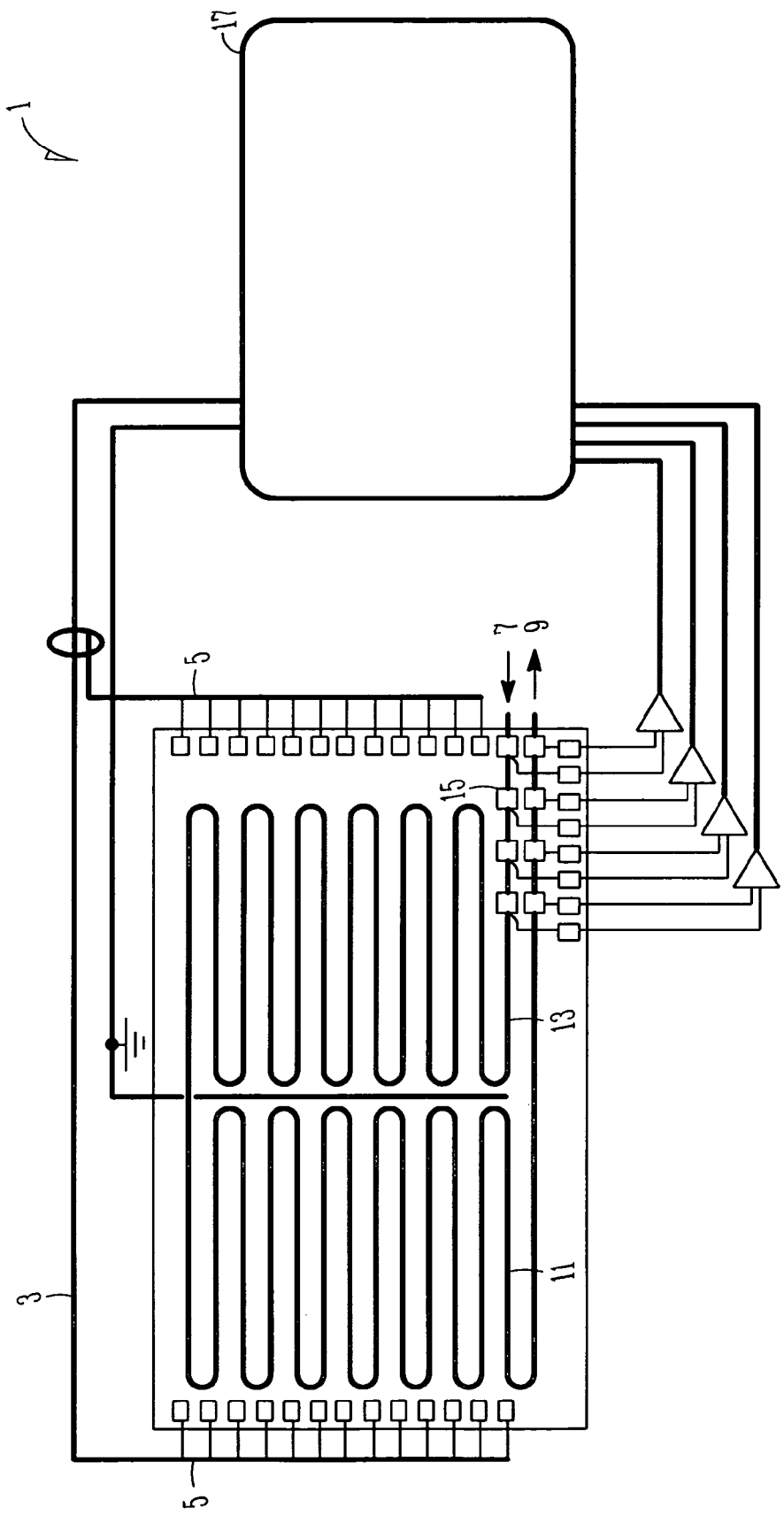
FIG. 1 illustrates a schematic diagram of a detector structure integrated in a micro analyzer, according to some embodiments of the invention.

Referring to FIG. 1, a schematic diagram illustrating a detector structure integrated in a micro analyzer is shown, according to some embodiments of the invention. A micro analyzer 1, such as a micro gas chromatograph (GC), utilizes an array of heaters 3 to heat the sample to a specified temperature. Contact pads 5 are positioned within the analyzer, such that they can transmit heat to the sample chamber, such as a column. The sample, such as a gas, enters the analyzer 1 through a sample inlet 7 and flows through a first series of detectors in a detector structure 15. The sample then moves through the microGC, which may consist of a channel or capillary column, for example. A pre-concentrator 13 may be utilized to increase the concentration of desirable species contained in the sample, thus allowing for a more sensitive detection of such species within the sample. A separator 11, separates the sample into its gaseous components depending on their physical or chemical properties. The separator may also consist of a micro-channel or a capillary column. As the sample flows toward the exit 9, it passes a matching second series of detectors in the detector structure 15. The first series and second series of detectors contain at least one pair of matching detectors. Such things as temperature, pressure, sample flow, space and stray capacitance can be controlled or normalized by comparing the readings from the first series of detectors positioned in the entrance of the sample chamber to the readings from the second series of detectors positioned near the exit of the microGC. This positioning of detectors helps to isolate the important variables of sample composition and quantity while eliminating most forms of noise and interference. Such monitoring and controls as microprocessors, A/D converters, pre-amplifiers, timers, heater controls and detector input power are represented by box 17.

Figure 2:
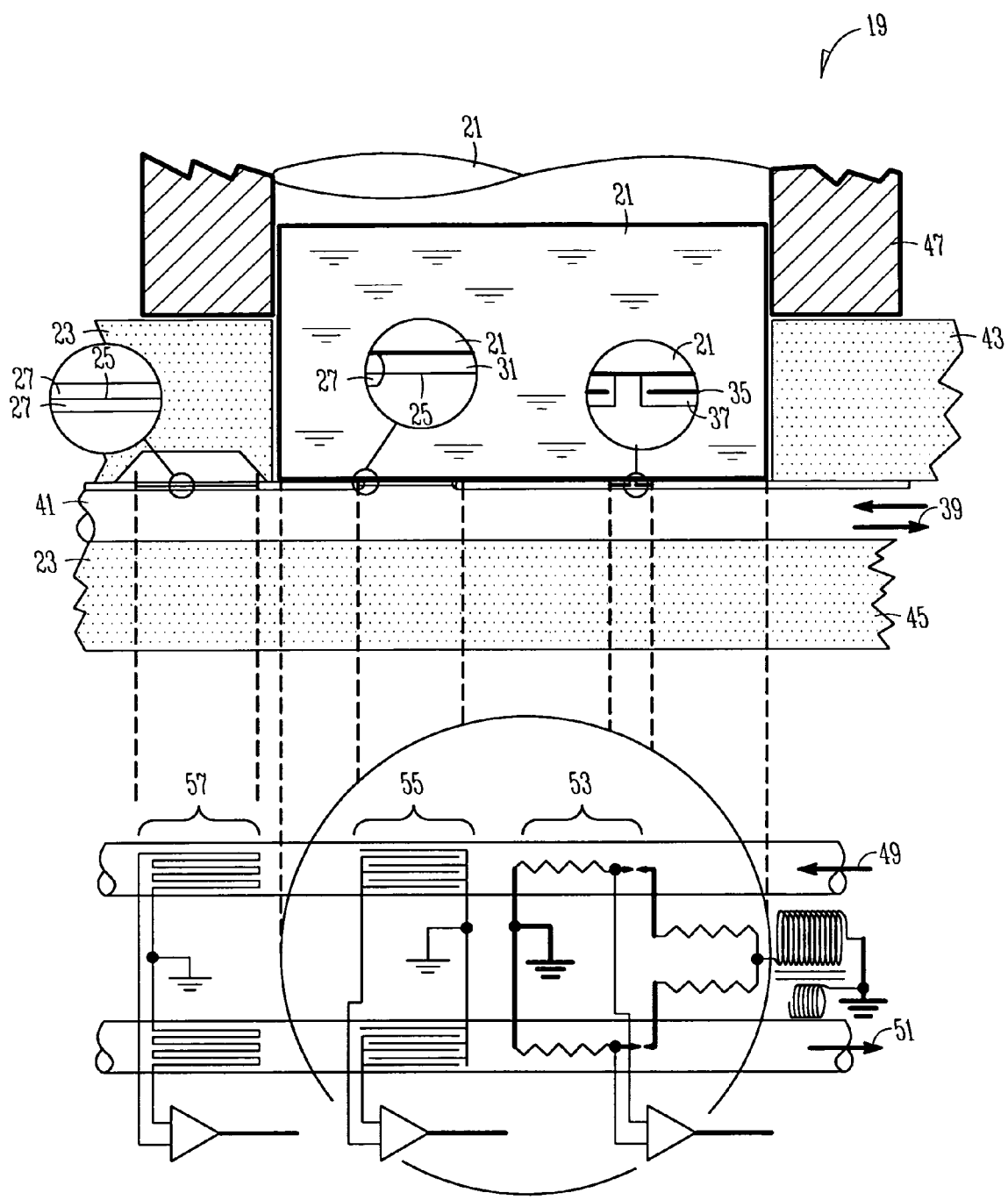
FIG. 2 illustrates a cross-sectional view of a detector structure integrated in a micro analyzer, according to some embodiments of the invention.

Referring to FIG. 2, a cross-sectional view of a detector structure integrated in a micro analyzer is shown, according to some embodiments of the invention. The cross-sectional view of the detector structure 19 illustrates the positioning of a vacuum ultra violet (VUV) photon source 21 in proximity to the sample channel 41 in which a sample flows 39. The sample channel 41 comprises the inlet 49 and outlet 51 for a sample in which a first and second series of detectors are positioned. The expanded view of the sample channel 41 shows the first and second series of detectors, such as a differential thermal conductivity detector (TCD) 57, a differential photo ionization detector (PID) 55 and a differential microdischarge detector (MDD), as examples. The TCD 57 and PID 55 utilize an ionizable metal 25, such as platinum, and silicon nitride 27 as an exemplary structural material. The sample 31, such as a gas, is shown in the PID expanded view. In reference to the MDD expanded view, aluminum 35 makes up part of the structure of the detector in which the silicon oxide and magnesium oxide plasma 37 surround. The channel wafer 45 and heater wafer 43 may comprise material such as silicon, pyrex or polymer 23, for example. A structural support material 47 is also shown.

The VUV energy source 21 is positioned adjacent to and can provide ions and electrons for such detectors as a PID 55 or MDD 53, for example. Other examples of detectors capable of utilizing the VUV energy source are electron capture detectors (ECD), ion/differential mass spectrometers (IMS/DMS), and ion trap mass spectrometers (ITMS). As shown in the figure, the TCD 57 and implicitly included chemical impedance detector (CID) are positioned outside the effective zone of the VUV energy source 21.

Figure 3:
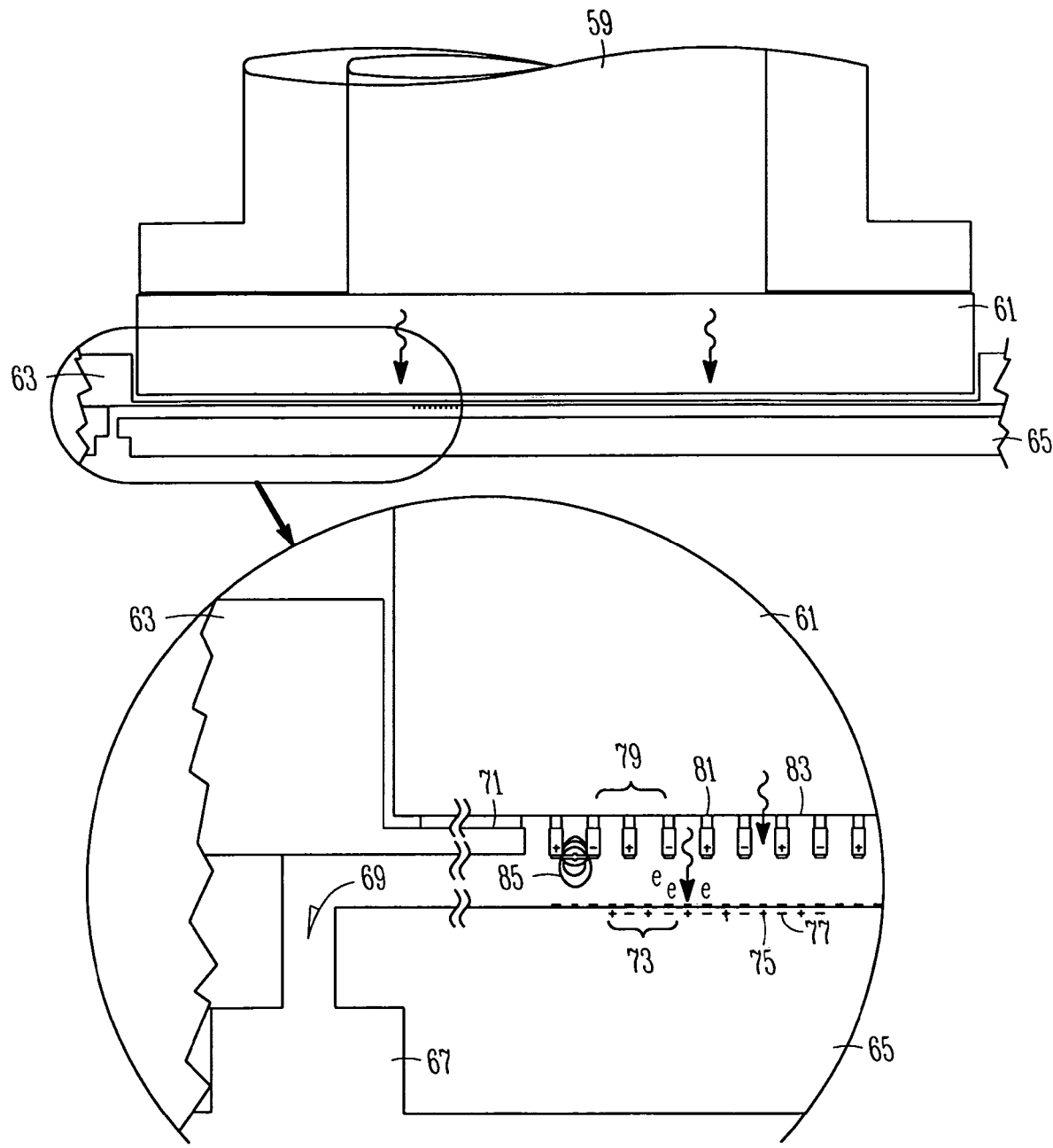
FIG. 3 illustrates a cross-sectional view of a PID/ECD detector structure integrated in a micro analyzer, according to some embodiments of the invention.

Referring to FIG. 3, a cross-sectional view of a PID/ECD detector structure integrated in a micro analyzer is shown, according to some embodiments of the invention. The figure shows how a PID 79 and ECD 73 can be integrated under one VUV lamp 59. The interdigitated electrodes 81, 83 on the side of the sample channel 69 can be spaced so that they penetrate the electron field into the channel. The positive 81 and negative 83 electrodes may penetrate up to 50% of the sample channel 69 diameter, for example. Further, the electrodes 81, 83 may penetrate 30-75% of the sample channel 69 diameter. The PID 79 collects all the charge-carrier pairs generated by the photons 85, so that an increase in photo-ionization current is indicative of higher analyte concentrations. The electrodes 81, 83 may be coplanar and the gaps between electrodes 81, 83 are no larger than 30-50% of the height of the sample channel 69, so that collecting the photo-ions and electrons by the electron field is predominantly from about the first 60% of the channel diameter that is proximate to the VUV lamp window 61.

The ECD 73 uses photo-electrons generated near the bottom of the sample channel 69 as they are knocked off the electrode 81, 83 metal and collected by the bottom set of interdigitated electrodes 75, 77. When an electron-attracting analyte flows by with a greater affinity for electrons than oxygen, it may capture such electrons and thus reduce the measurable ECD current. Metal film strips of negative polarity 77 are positioned on the bottom of the sample channel 69 and are in the path of the VUV photons emerging from between the PID electrodes 81, 83. The photo-electrons knocked out of the metal can normally be measured as a "null" current, which decreases when such electrons are "captured" (as mentioned above) by passing analyte molecules and dragged or carried away by the sample. Such decreases indicate an ECD signal about the presence, identity (by its microGC elution time) and concentration of an analyte.

In addition to the merged PID and ECD function, the micro analyzer may also include an ion trap mass spectrometer (ITMS). The ions to be trapped may preferentially be generated by the VUV source. Further, ions may be generated in close proximity to the ITMS by capturing photoelectrons from its own metal electrodes. Ions can also be provided by the VUV lamp for operation of MDD and IMS/DMS in addition to the merged PID and ECD.

Figure 4:
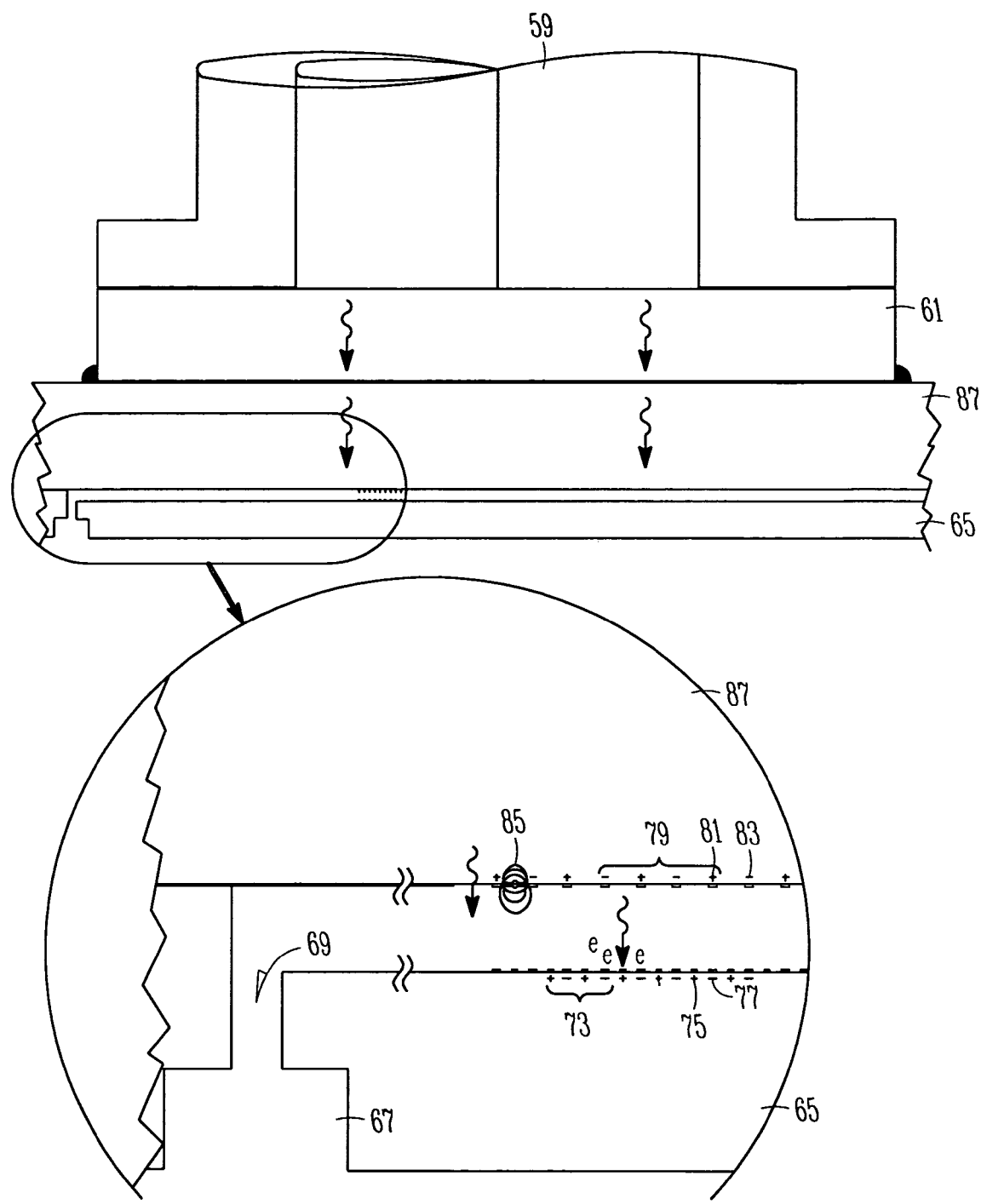
FIG. 4 illustrates a cross-sectional view of a PID/ECD detector structure integrated in a micro analyzer, according to some embodiments of the invention.

A channel wafer 65 and heater wafer 63 provide structural support for the micro analyzer and its detectors. A material suitable for transmitting the energy from the VUV lamp 59 comprises the window 61, such as magnesium fluoride or lithium fluoride. A recess 67 optionally provides for a capillary attachment. A membrane 71 acts as a structural connects the heater wafer 63 and window 61. The membrane 71 may be comprised of SU-8 composite or polydimethylsiloxane (PDMS), for example. FIG. 4 represents an embodiment similar to FIG. 3 with the exception that the window 61 is now positioned adjacent to an electrode wafer 87. The electrode wafer 87 must transmit the VUV energy and be made of materials such as magnesium fluoride or lithium fluoride. The electrodes 81, 83 of the PID may then be recessed into the electrode wafer 87. This positioning allows for more versatility and simplicity in manufacturing of the micro analyzer.

For all figures shown, the VUV light may be positioned adjacent to the detector structure such that the detection signal is maximized before the VUV light is absorbed by air and the generated ions and electrons have recombined. The order of detectors may be of importance as the best analyte readings will come if the detectors are exposed to the most pristine analyte possible. Therefore, the non-ionizing, non-destructive detectors, such as a TCD and CID, are located in a parallel side-stream or upstream the sample channel from the location of the detectors requiring ions (and possible sample gas component fragmentation) for operation, such as a PID, ECD, IMS/DMS, ITMS and MDD. In one example of a possible configuration, the inlet stream could be split such that a series of one or more ionizing, or destructive, detectors are positioned in one branch and another series of one or more non-destructive detectors are positioned in another branch of the inlet. After passing through the non-destructive detectors, the sample would pass through the analyzer and then a second series of paired detectors near the sample exit. The sample passing through the inlet branch containing the destructive detectors would then be routed directly to the paired series of detectors positioned near the sample exit, without passing through the analyzer. In situations where the destroyed fraction of the sample is less than about 1%, it may not be necessary to separate the destructive and non-destructive detectors.

Figure 5:
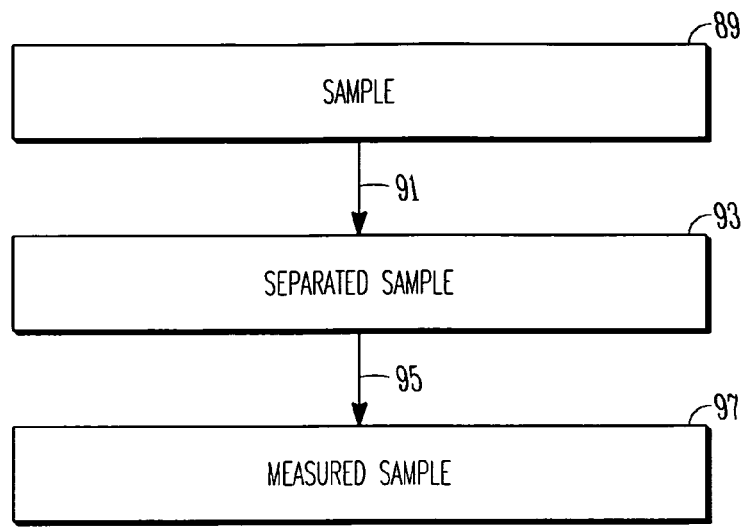
FIG. 5 illustrates a block flow diagram of a method to analyze a sample, according to some embodiments of the invention.
Figure 6:
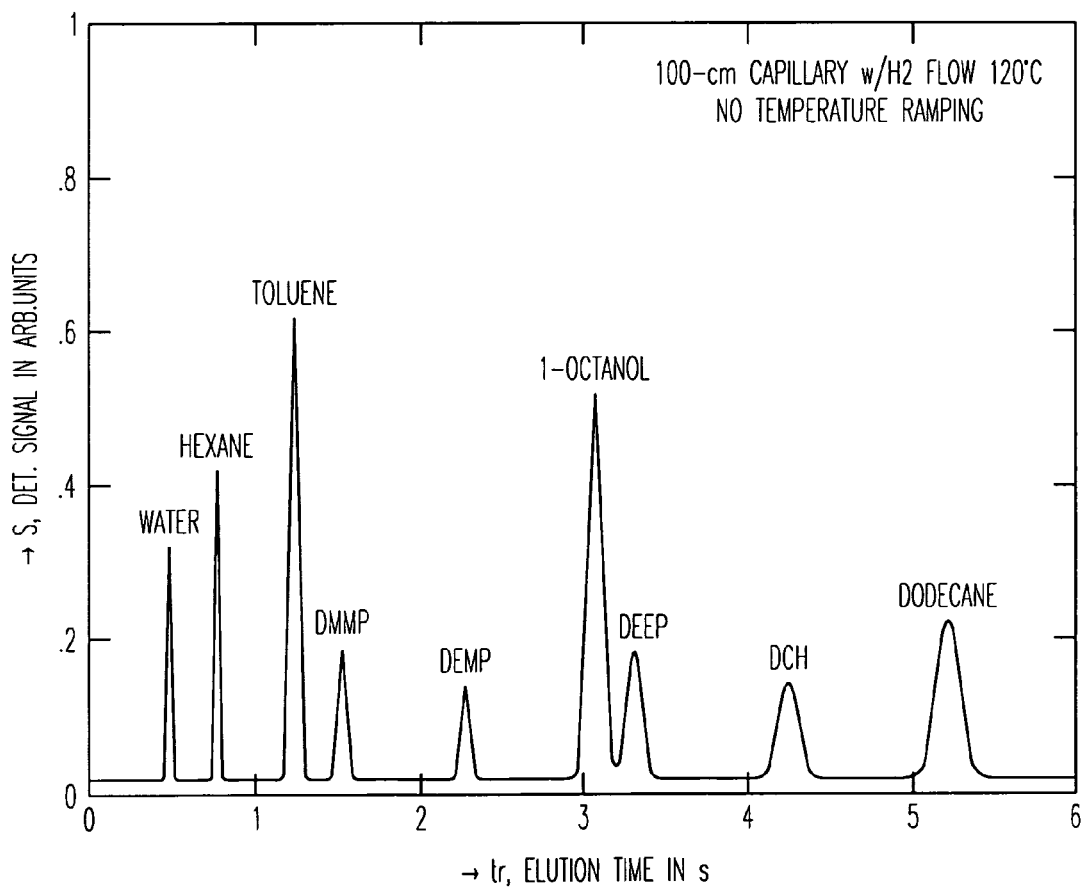
FIG. 6 illustrates a graphical view of a gas chromatograph readout produced by a micro analyzer, according to some embodiments of the invention.

Referring to FIG. 5, a block flow diagram of a method to analyze a sample is shown, according to some embodiments of the invention. A sample 89 flows 91 into a sample channel and may be separated. The sample 89 can be a gas and the sample channel may comprise a separator. The separator may be a gas chromatography column and can separate the components of the sample based on physical properties, chemical properties or both, as illustrated in FIG. 6. Referring back to FIG. 5, the separated sample 93 is contacted 95 with a PID and ECD in which a VUV source is an ionization source for both detectors. The measured sample 97 is then produced. Optionally, the sample may be contacted with another pair of PID/ECDs as it flows into the sample channel. Other detectors may be used alone or in pairs either upstream or downstream of the PID/ECD location in the sample flow. The VUV-generated ions may also serve as charge carriers in ion-drag pumps, in which ions forced to drift between an applied field drag along (via viscous drag) neutral molecules and thus provide a useful pumping action needed to move the sample gas through the micro gas analyzer.

The Abstract is provided to comply with 37 C.F.R. §1.72(b) to allow the reader to quickly ascertain the nature and gist of the technical disclosure. The Abstract is submitted with the understanding that it will not be used to interpret or limit the scope or meaning of the claims.

The invention claimed is:

1. An integrated detector structure comprising:
a photo-ionization detector (PID);
an electron capture detector (ECD);
a vacuum ultra violet (VUV) source, wherein the VUV source is an ionization source for both the PID and ECD and wherein the PID and ECD are integrated under the VUV source, and a sample channel with sample inlet and sample outlet, the PID at a first location within the sample channel and the ECD at a second location within the sample channel, and wherein the ion and electron pairs created by the photoionization within the sample channel are collected by the PID electrodes and wherein photoelectrons that are knocked off by the PID electrodes are subsequently collected by the ECD electrodes.

2. The detector structure of claim 1, further comprising in addition to the PID and ECD, one or more detectors positioned to use the VUV source as an ionization source.

3. The detector structure of claim 2, wherein the one or more detectors comprise a microdischarge detector (MDD), a ion mobility spectrometer (IMS), an differential mobility spectrometer (DMS), a ion trap mass spectrometer (JTMS) or combinations thereof.

4. The detector structure of claim 1, further comprising one or more non-ionizing detectors and pumps.

5. The detector structure of claim 4, wherein the non-ionizing detectors are positioned in relation to a sample flow such that they contact a sample before the sample contacts any other detectors.

6. An integrated micro analyzer, comprising:
a sample inlet, wherein a sample enters the micro analyzer;
a sample channel, wherein the sample is contained and flows through the micro analyzer;
a sample exit, wherein the sample exits the micro analyzer;
a photo-ionization detector (PID), coupled at or near the sample exit at a first location within the sample channel;
an electron capture detector (ECD), coupled at or near the sample exit at a second location within the sample channel; and
a vacuum ultra violet (VUV) source, wherein the VUV source is an ionization source for the detectors, and wherein the PID and ECD are integrated under the VUV source, and wherein the ion and electron pairs created by the photoionization within the sample channel are collected by the PID electrodes and wherein photoelectrons that are knocked off by the PID electrodes are subsequently detected by the ECD electrodes.

7. The micro analyzer of claim 6, wherein the sample channel comprises a pre-concentrator to pass unwanted species from the sample and concentrate species of interest within a sample.

8. The micro analyzer of claim 6, wherein the sample channel comprises a separator to physically separate components of the sample in time.

9. The micro analyzer of claim 6, wherein the sample channel comprises a gas chromatography (GC) column.

10. The micro analyzer of claim 6, wherein a second PID and second ECD are coupled at or near the sample inlet.

11. The micro analyzer of claim 10, wherein a second VUV source is an ionization source for both the second PID and second ECD.

12. The micro analyzer of claim 6, further comprising in addition to the PID and ECD, one or more detectors coupled at or near the sample exit positioned to use the VUV source as an ionization source.

13. The micro analyzer of claim 12, wherein the one or more detectors comprise a microdischarge detector (MDD), a ion mobility detector (IMS), an differential mobility detector (DMS), a ion trap mass spectrometer (ITMS) or combinations thereof.

14. The micro analyzer of claim 6, further comprising one or more non-ionizing detectors coupled at or near the sample exit.

15. The micro analyzer of claim 14, wherein the non-ionizing detectors are positioned in relation to a sample flow such that they contact a sample before the sample contacts any other detectors at or near the sample exit.

16. The micro analyzer of claim 14, further comprising at least one parallel sample inlet in which the non-ionizing detectors are positioned and separated from the ionizing detectors.

17. An integrated micro analyzer, comprising:
a sample inlet, wherein a sample enters the micro analyzer;
a sample channel, wherein the sample is contained and flows through the micro analyzer;
a sample exit, wherein the sample exits the micro analyzer;
a photo-ionization detector (PID), coupled at or near the sample inlet and exit at a first location within the sample channel;
an electron capture detector (ECD), coupled at or near the sample inlet and exit at a second location within the sample channel;
a micro discharge detector (MDD), coupled at or near the sample inlet and exit;
an ion mobility spectrometer (IMS), coupled at or near the sample inlet and exit;

an ion trap mass spectrometer (ITMS), coupled at or near the sample inlet and exit;

a differential (ion) mobility spectrometer (DMS), coupled at or near the sample inlet and exit; and a vacuum ultra violet (VUV) source, wherein the VUV source is an ionization source for the above detectors, and wherein the PID, ECD, MDD, IMS, ITMS, and DMS are integrated under the VUV source, and wherein the ion and electron pairs created by the photoionization within the sample channel are collected by the PID electrodes and wherein photoelectrons that are knocked off by the PID are collected by the ECD, MDD, IMS, ITMS, and DMS electrodes.

18. A method for analyzing a sample, comprising:

flowing a sample into a gas chromatography (GC) sample channel, sufficient to separate the sample components;

contacting a sample with at least one PID and ECD, sufficient to measure the desired properties (elution time and concentration) of the sample components, wherein the PID and ECD utilize the same VUV source for ionization, and wherein the PID and ECD are integrated under the VUV source, and wherein the ion and electron pairs created by the photoionization within the sample channel are collected by the PID electrodes and wherein the photoelectrons that are knocked off by the PID are subsequently collected by the ECD electrodes.

19. The method claim 18, wherein prior to flowing the sample, contacting the sample with a first paired PID and ECD, wherein the PID and ECD utilize one VUV source for ionization.

20. The method of claim 18, wherein in addition to contacting a sample with at least one PID and ECD, the sample is contacted with at least one of a microdischarge detector (MDD), a ion mobility detector (IMS), an differential mobility detector (DMS), a ion trap mass spectrometer (JTMS), a combination thereof or one or more ion gas pumps.

* * * * *